United States Patent [19]

Fukushima et al.

[11] Patent Number: 4,687,762

[45] Date of Patent: Aug. 18, 1987

[54] WATER SOLUBLE DRUG COMPLEX AND METHOD FOR PRODUCTION OF SAME

[75] Inventors: Tsunekazu Fukushima, Hyogo; Hiroshi Emoto, Osaka; Yoshio Kagitani, Nara; Kazumasa Yokoyama; Masayuki Nishida, both of Osaka; Tadakazu Suyama, Kyoto, all of Japan

[73] Assignee: Green Cross Corporation, Osaka, Japan

[21] Appl. No.: 716,436

[22] Filed: Mar. 27, 1985

[30] Foreign Application Priority Data

Mar. 31, 1984 [JP] Japan .................... 59-63994

[51] Int. Cl.⁴ .............. A61K 31/70; A61K 31/685; A61K 31/545
[52] U.S. Cl. .......................... 514/34; 514/37; 514/78; 514/220; 514/573
[58] Field of Search .............. 514/78, 37, 34, 220, 514/573

[56] References Cited

U.S. PATENT DOCUMENTS

| | | | |
|---|---|---|---|
| 4,196,202 | 4/1980 | Okoida | 514/78 |
| 4,239,754 | 12/1980 | Sache et al. | 514/78 |
| 4,328,222 | 5/1982 | Schmidt | 514/221 |
| 4,372,949 | 2/1983 | Kodama et al. | 514/78 |
| 4,377,567 | 3/1983 | Geho | 514/78 |
| 4,411,894 | 10/1983 | Schrank et al. | 514/221 |
| 4,880,041 | 10/1984 | Myles et al. | 436/508 |

FOREIGN PATENT DOCUMENTS

| | | | |
|---|---|---|---|
| 011745 | 6/1980 | European Pat. Off. | 514/221 |
| 0084898 | 8/1983 | European Pat. Off. | 514/78 |
| 2656333 | 6/1978 | Fed. Rep. of Germany | 514/78 |
| 2390159 | 12/1978 | France | 514/221 |
| 0093909 | 6/1982 | Japan | 514/78 |

OTHER PUBLICATIONS

Gibbes et al., Biochemistry, vol. 16, No. 12, (1977), pp. 2806–2810.

Primary Examiner—Johnnie R. Brown
Assistant Examiner—John W. Rollins
Attorney, Agent, or Firm—Sughrue, Mion, Zinn, Macpeak & Seas

[57] ABSTRACT

The invention provides a method of producing a water-soluble complex comprising a water-insoluble drug and a phospholipid, comprising the steps of (1) dissolving a water-insoluble drug and a phospholipid in an organic solvent, (2) removing the solvent to leave behind a drug-containing phospholipid film, (3) suspending the resulting film in an aqueous solution, (4) ultrasonicating the film, (5) centrifuging the resulting suspension, and (6) recovering the lowermost layer of the resulting sediment to yield the water-soluble complex. The above complex can be administered parenterally as well as by the oral and other routes, and is so rich in the drug component that a remarkably increased drug activity can be realized.

29 Claims, No Drawings

WATER SOLUBLE DRUG COMPLEX AND METHOD FOR PRODUCTION OF SAME

FIELD OF THE INVENTION

This invention relates to a water-soluble drug complex comprising a water-insoluble drug with a phospholipid and to a method of producing the same.

BACKGROUND OF THE INVENTION

The so-called insoluble drugs which are insoluble or only sparingly soluble in water and organic solvents are generally difficult to formulate into pharmaceutical preparations. Thus, they are usually made into administrable forms by such techniques as emulsification, clathration, preparation of soluble derivative, entrapping in liposomes, microencapsulation, or the like. However, even by such procedures it is generally still difficult to obtain preparations that would allow the drug to display its action fully.

The present inventors conducted an intensive study to develop a method of solubilizing such drugs and processing them into useful pharmaceutical preparations. The study led to the present invention, i.e., the finding that if a drug-containing phospholipid film, prepared by a process similar to that employed in liposome-producing technology is suspended in an aqueous solution, ultrasonicated and centrifuged, there is obtained a fraction rich in said water-insoluble drug in the lowermost layer of the sediment and that this fraction comprises a drug-phospholipid complex which is water-soluble and very useful as a pharmaceutical product.

SUMMARY OF THE INVENTION

It is an object of this invention to provide a method of solubilizing water-insoluble drugs.

It is another object of this invention to provide a method of producing a drug-phospholipid complex which is soluble in water and rich in the drug.

It is a further object of this invention to provide a novel water soluble pharmaceutical product.

Further object and advantages of this invention will become apparent from the following detailed description of the invention.

DETAILED DESCRIPTION OF THE INVENTION

The above-mentioned objects of this invention have been met by a method comprising the steps of (1) dissolving (A) a water-insoluble drug and (B) a phospholipid in an organic solvent, (2) removing the organic solvent therefrom to leave behind a drug-containing phospholipid film, (3) suspending the resulting film in an aqueous solution, (4) subjecting the suspension to ultrasonic treatment, (5) centrifuging the resulting suspension, and (6) recovering the lowermost layer of the sediment to yield a drug-phospholipid complex which is soluble in water and rich in the drug.

The water-insoluble drug is a pharmaceutically active substance whose solubility in water is preferably not higher than 0.1 mg/ml. Such a drug is preferably a low molecular weight compound, more preferably having a molecular weight not over 1000. Most preferably, said drug is a compound whose solubility in common organic solvents, such as chloroform, ethyl acetate, acetone, ether, benzene, etc., is approximately 0.1 to 100 mg/ml. Examples of such drug include anticancer drugs such as spadicomycin, anthramycin, fluorouracil, daunomycin, adriamycin, etc., anti-inflammatory and analgesic drugs such as flurbiprofen, acemetacin, etc., prostaglandins, lipoxygenase inhibitors, etc.

The phsopholipid as a component of said water-insoluble drug-phsopholipid complex is any of known physiologically acceptable and metabolizable non-toxic phospholipids. For example, phosphatidylcholine, phosphatidylserine, phosphatidylic acid, phosphatidylglycerin, phosphatidylethanolamine, phosphatidylinositol, sphingomyelin, dicetyl phosphate, lysophosphatidylcholine (lysolecithin), stearylamine, etc. as well as mixtures of phospholipids such as soybean phospholipid, egg yolk phospholipid, etc. Preferred phospholipids include soybean and egg yolk phospholipids.

Using the two components, i.e. water-insoluble drug and phospholipid, the complex according to this invention is produced. First, the phospholipid and water-insoluble drug are dissolved in an organic solvent such as chloroform. As to the amounts of the two components, the preferred ratio is 0.01 to 10 parts by weight, preferably 0.02 to 0.1 parts by weight of the water-insoluble drug to each part by weight of the phospholipid. From the resulting mixture of drug and phospholipid in a vessel, the solvent is evaporated preferably under reduced pressure in a rotary evaporator at 20° to 30° C. for 5 to 10 minutes to remove 100 ml of the solvent, whereby a thin drug-containing phospholipid film is formed on the internal wall of the vessel. In this procedure, for improved stability of the phospholipid, an antioxidant such as $\alpha$-tocopherol is preferably added at the level of 0.001 to 1.0% by weight, preferably 0.01 to 0.1% by weight relative to the weight of the phospholipid. Of course, other known stabilizers may also be added, such as albumin, dextran, polyvinylpyrrolidone, gelatin, hydroxylethyl starch, and nonionic surfactants.

Then, to this thin film is added a physiologically acceptable aqueous solution (an aqueous solution adjusted to pH 5.5 to 8, preferably pH 6 to 7, such as citrate buffer, acetate buffer, phosphate buffer, physiological saline solution, etc.) at a level of 10 to 500 ml per gram of the phospholipid, followed immediately by shaking or stirring to disintegrate the film and to thereby produce particles of said drug-phospholipid complex. The general procedure may be putting several glass beads (particle diameter: 1 to 10 mm) in a round-bottomed vessel and shaking the vessel vigorously at room temperature for 3 to 20 mintues. In this described manner, a suspension of the complex in a concentration range of 0.5 to 100 mg phospholipid/ml is prepared.

The above particles are then subjected to ultrasonic treatment (output: 10 to 100 W, 10 minutes to 2 hours), whereby the particle diameter is adjusted to 0.2 to 2$\mu$, preferably 0.3 to 1.0 $\mu$. To prevent generation of heat (increase of the liquid temperature) during the procedure, this ultrasonic wave treatment is carried out under ice-cooling and preferably in an inert atmosphere such as nitrogen gas.

The ultrasonicated suspension is then centrifuged at 10,000$\times$ g or more, preferably 20,000 to 30,000$\times$ g, for about 30 minutes to 2 hours, at a temperature of 5° to 20° C.

As a result, the suspension is divided into 3 layers. The upper layer (Fraction I) is a supernatant having the color of the phospholipid and corresponds to the conventional liposomes or small unilamellar vesicles. The intermediate layer (Fraction II) is a sediment with the mixed color of the drug and phospholipid and is a layer of phospholipid particles not disrupted by ultrasonication. By further ultrasonication of this Fraction II, it can be converted to Fraction I and Fraction III which is described below. The bottom or lowermost layer (Fraction III) is a sediment whose color corresponds to that of the drug. This lowermost layer Fraction III is recovered and preferably washed centrifugally with a physiologically acceptable aqueous solution referred to hereinbefore, an aqueous phospholipid solution, or the above-mentioned supernatant Fraction I, whereby the desired drug-phospholipid complex is obtained as pellets or a suspension. The properties of the complex thus obtained are set forth hereinafter in Experimental Example 1.

The drug-phospholipid complex according to this invention can be processed into a variety of pharmaceutical preparations or dosage forms by conventional pharmaceutical procedures. Liquid preparation so produced may be freeze-dried to provide lyophilized preparations. In this procedure a suitable known stabilizer may be used according to the drug or/and phospholipid. The addition of a nonionic surfactant (e.g., polyalkylene glycol-polyoxyalkylene copolymers, hydrogenated castor been oil-polyoxyalkylene derivatives, and caster bean oil-polyoxyalkylene derivatives) contributes to an increased solubility of the lyophilizates. Such lyophilized preparations would generally be reconstituted by dissolution or dilution with a physiologically acceptable aqueous solution such as physiological saline or said Fraction I but may be formulated into tablets, capsules, enteric-coated tablets, suspension, granules, powders, injections suppositories, etc. by conventional pharmaceutical procedures.

The drug-phospholipid complex according to this invention has an increased solubility in water as compared with the component water-insoluble drug, and exhibits activity a few times to several tens of times higher than the activity displayed by the water-insoluble drug. Moreover, as the toxicity of the drug is also reduced as compared with the case in which the same drug is administered alone, a potentiation of drug efficacy can be realized through increase of the dosage.

In addition, water-insoluble drugs can be provided in the form of injectable products. Thus, by controlling the particle size of the complex to the range of 0.2 to 2μ, the complex can be administered intravenously to realize a fast-acting effect or an improved tissue or local affinity. Moreover, gastrointestinal side effects accompanying oral medication can be prevented and an increased efficacy through increased gastrointestinal absorption can be obtained.

The drug-phospholipid complex thus provided by this invention enables pharmaceutical manufacturers to provide new effective pharmaceutical products using water-insoluble drugs, and promises new developments in the medical industry and clinical medicine.

Having thus described this invention in general, the inventors present the following experimental, working and control examples for assisting a further understanding of the invention. It should be understood that the working examples given are only illustrative and by no means limitative of the invention.

EXPERIMENTAL EXAMPLE 1

Physicochemical Properties of the Complex (1) Incorporation of the Drug

The precentage incorporation of the drug in each of the layers (Fractions I, II and III) after centrifugation was investigated. Each layer was separated and treated with Triton X-100 (1.0% by volume) to disrupt the complex. The disrupted complex was suspended in a 50 mM phosphate buffer (pH 7.0) and centrifuged at 20000× g at room temperature for 1 hours, and the supernatant was recovered and the drug therein was assayed by high performance liquid chromatography. From the result, the percent incorporation of the drug (drug/phospholipid, w/w %) was calculated. The percentage incorporation values of various water-insoluble drugs are shown in Table 1.

TABLE 1

| | Percent Incorporation (w/w %) | | |
|---|---|---|---|
| | Fraction I | Fraction II | Fraction III |
| Daunomycin | 100 | 210 | 458 |
| Spadicomycin* | 50 | 1020 | 1800 |
| Adriamycin | 2.4 | 20.0 | 860 |
| 5-Fluorouracil | 10.2 | 40.5 | 1020 |
| Dexamethasone | 105 | 120 | 330 |
| Flurbiprofen | 0.45 | 170 | 2070 |
| Acemetacin | 14 | 225 | 485 |
| Prostaglandin $E_1$ | 0.8 | 120 | 990 |

*The trademark of Green Cross Corporation

It is clear that Fraction III shows a remarkably high degree of drug incorporation and is thus useful as the complex according to this invention.

(2) Particle Size

The particle size of each of Fractions I, II and III was determined by centrifugal sedimentation analysis (Coulter counter method). The results are shown in Table 2.

TABLE 2

| | Center Particle Diameter ($\mu$) | | |
|---|---|---|---|
| | Fraction I | Fraction II | Fraction III |
| Daunomycin | <0.35 | 0.95 | 0.45 |
| Spadicomycin | <0.35 | 1.20 | 0.48 |
| Adriamycin | <0.35 | 1.08 | 0.45 |
| 5-Fluorouracil | <0.35 | 0.65 | 0.45 |
| Dexamethasone | <0.35 | 0.88 | 0.50 |
| Flurbiprofen | <0.35 | 0.70 | 0.45 |
| Acemetacin | <0.35 | 0.90 | 0.48 |
| Prostaglandin $E_1$ | <0.35 | 2.00 | 0.55 |

(3) Solubility

The solubility of each drug-phospholipid complex according to this invention in distilled water for injection (water temperature 20° C.) was compared with that of the component drug. The results are shown in Table 3.

TABLE 3

| | Solubility (mg/ml) | |
|---|---|---|
| | Component Drug | Complex of This Invention |
| Daunomycin | 20 | 108 |
| Spadicomycin | 55 | 440 |
| Adriamycin | 7 | 92 |
| 5-Fluorouracil | 13 | 680 |
| Dexamethasone | 0.05 | 3.0 |
| Flurbiprofen | 0.15 | 0.9 |
| Acemetacin | 0.40 | 6.5 |
| Prostaglandin $E_1$ | 0.07 | 5.6 |

It is apparent that the composing of a water-insoluble drug with a phospholipid in accordance with this invention resulted in a marked improvement in water solubility.

(4) Stability of Particle Size

Drug-phospholipid complexes were prepared in accordance with the procedure of Example 1 and each of the complexes was dissolved in distilled water for injection to give a 0.5% (w/v) aqueous solution. This solution was stored at 4° C. for 1 month and the particle size was measured to investigate the stability of particle size. The results are set forth in Table 4.

TABLE 4

|  | Particle Size of Complex (μ) | |
| --- | --- | --- |
|  | Immediately After Production | After Storage at 40° C. for 1 Month |
| Daunomycin | 0.45 | 0.44 |
| Spadicomycin | 0.48 | 0.52 |
| Adriamycin | 0.45 | 0.45 |
| 5-Fluorouracil | 0.45 | 0.48 |
| Dexamethasone | 0.50 | 0.60 |
| Flurbiprofen | 0.45 | 0.63 |
| Acemetacin | 0.48 | 0.42 |
| Prostaglandin $E_1$ | 0.55 | 0.78 |

(5) Stability of the Complex

For the purpose of investigating the stability of drug-phospholipid complexes, each complex was either suspended in physiological saline solution and allowed to stand at room temperature (13°–26° C.) for 1 week (Test A) or incubated in human plasma at 37° C. for 1 hour (Test B). In both Test A and Test B, each aged complex was treated in a manner similar to Experimental Example 1 (1) Incorporation of the Drug. Thus, the complex was first centrifuged and the sediment was centrifugally washed with physiological saline 3 to 4 times, followed by treatment with Triton X-100 (1.0% by volume). The drug thus brought into an aqueous solution was assayed by high performance liquid chromatography and the stability of the complex was evaluated from the residual amount of the drug. The results are set forth in Table 5.

TABLE 5

|  | Residual Amount of Drug (%) | |
| --- | --- | --- |
|  | (A) | (B) |
| Daunomycin | 98 | 88 |
| Spadicomycin | 101 | 97 |
| Adriamycin | 89 | 95 |
| 5-Fluorouracil | 103 | 101 |
| Dexamethasone | 98 | 98 |
| Flurbiprofen | 95 | 92 |
| Acemetacin | 95 | 78 |
| Prostaglandin $E_1$ | 96 | 79 |

Each figure in the above table represents the percentage residue with the amount of the unaged complex being taken as 100%.

EXPERIMENTAL EXAMPLE 2

The intravenous and oral acute toxicity values ($LD_{50}$) in mice of each drug-phospholipid complex of this invention were compared with those of the corresponding component drug. The results are shown in Table 6.

TABLE 6

|  | Acute Toxicity (mg/kg) | | | |
| --- | --- | --- | --- | --- |
|  | Intravenous Administration | | Oral Administration | |
|  | Drug | Complex | Drug | Complex |
| Daunomycin | 23.5 | 33.1 | 271.4 | 445.7 |
| Adriamycin | 9.1 | 15.7 | 736.9 | 2104 |
| 5-Fluorouracil | 173.4 | 231.4 | 249.1 | 437.6 |

TABLE 6-continued

|  | Acute Toxicity (mg/kg) | | | |
| --- | --- | --- | --- | --- |
|  | Intravenous Administration | | Oral Administration | |
|  | Drug | Complex | Drug | Complex |
| Prostaglandin $E_1$ | — | — | 7566 | 9737 |

EXPERIMENTAL EXAMPLE 3

The pharmacologic effect of the drug-phospholipid complex according to this invention administered by the intravenous route was compared with that of the component drug administered in the same manner using 10 aminals. The results are shown in Table 7. Test (1): Antitumor Effect Ten male $BDF_1$ mice (1–20 g) were inoculated with $10^6$ cells of L-1210 mouse ascites tumor cells. After 24 hours from the inoculation Sapdicomycin as a drug was administered to the animals for continuous 5 days, and the number of days in which the test animals were dead. The life prolongation ratio was calculated according to the following equation.

$$\text{Life Prolongation Ratio (\%)} = \frac{A_2 - A_1}{A_1} \times 100$$

wherein $A_1$ represents an average survival period (day) of control group (without administration) and $A_2$ represents that of administered group.

Test (2): Blood Pressure Lowering Effect

Ten normal male mongrel dogs were intravenously administered with prostaglandin $E_1$ and the blood pressure of each animal was measured using a catheter inserted into the carotid artery of the animal.

The blood pressure lowing ratio was calculated according to the following equation.

$$\text{Blood Pressure Lowering (\%)} = \frac{P_1 - P_2}{P_1} \times 100$$

wherein $P_1$ represents the blood pressure after the administration and $P_2$ represents that before the administration.

TABLE 7

|  | Drug | | Complex | |
| --- | --- | --- | --- | --- |
|  | Dosage (mg/kg) | Effect (%) | Dosage (mg/kg) | Effect (%) |
| Test (1) | 2.5 | 19 | 2.5 | 24 |
|  | 5.0 | 25 | 5.0 | 31 |
|  | 10.0 | 50 | 10.0 | 68 |
| Test (2) | 0.25 | 4.8 | 0.25 | 5.4 |
|  | 0.5 | 7.7 | 0.5 | 9.3 |
|  | 1.0 | 10.5 | 1.0 | 11.6 |

EXPERIMENTAL EXAMPLE 4

The organ affinity of the drug-phospholipid complex according to this invention was compared with that of the component drug. The results are shown in Table 8.

Ten male Wistar rats inoculated with Walker solid carcinosarcoma cells were used as test animals and $1.8 \times 10^7$ dpm/kg of the $^3H$-labeled drug was intravenously administered. Twenty-four hours after the administration, the degree of retention of the drug in each organ was estimated by determining the radio-activity level.

TABLE 8

| Spadicomycin | dpm per Gram Organ Weight | |
| --- | --- | --- |
| | Intravenous Injection of Drug | Intravenous Injection of Complex |
| Whole Blood | 825 | 956 |
| Liver | 585 | 631 |
| Kidney | 129 | 135 |
| Tumor | 3800 | 6310 |

EXPERIMENTAL EXAMPLE 5

The oral route absorption of the drug-phospholipid complex according to this invention administered was compared with that of the component drug similarly administered.

Ten male Wistar rats inoculated with Walker solid carcinosarcoma cells were used as test animals and $1.8 \times 10^7$ dpm/kg of the $^3$H-labeled drug was intravenously administered. Twenty-four hours after the administration, the degree of retention of the drug in each organ was estimated by determining the radio-activity level. The results are set forth in Table 9.

TABLE 9

| | Absorption Rate (%)* | |
| --- | --- | --- |
| | Drug | Complex |
| 5-Fluorouracil | 53 | 66 |
| Spadicomycin | 2.0 | 16 |

*The dosage was taken as 100%.

EXAMPLE 1

In 100 ml of chloroform were dissolved 0.25 g of spadicomycin, 10 g of purified egg yolk phospholipid and 10 mg of α-tocopherol, and the chloroform was distilled off under reduced pressure in a rotary evaporator, whereby a thin spadicomycin-containing phospholipid film was prepared. To this vessel was added 100 ml of a 50 mM phosphate buffer containing 50 mM of sodium chloride (pH 7.0) and after placement of glass beads, the vessel was immediately shaken vigorously at room temperature for 20 minutes. Using a Branson Sonic Power Cell Disruptor #350 (output 60 W), the above suspension was ultrasonicated under ice-cooling for 1 hour. Then, at room temperature, the disrupted suspension was centrifuged at 25,000× g for 1 hour and the bottom sediment was recovered and centrifugally washed several times with the same buffer as above followed by filtration through a bacterial filter. The above procedure gave pellets of spadicomycin-phospholipid complex.

EXAMPLE 2

The complex pellets obtained in Example 1 were freeze-dried to give a lyophilized spadicomycin-phospholipid complex.

EXAMPLE 3

The procedure of Example 1 was repeated except that 0.5 g of daunomycin was used in lieu of 0.25 g of spadicomycin, whereby pellets of daunomycin-phospholipid complex were obtained.

EXAMPLE 4

The procedure of Example 1 was repeated except that 0.4 g of 5-fluorouracil was used in lieu of 0.25 g of spadicomycin, whereby pellets of 5-fluorouracil-phospholipid complex were obtained.

EXAMPLE 5

The procedure of Example 1 was repeated except that 0.25 g of dexamethasone was used in lieu of 0.25 g of spadicomycin, whereby a dexamethasone-phospholipid complex was obtained.

EXAMPLE 6

The same procedures as Examples 1 and 2 were repeated except that 0.5 g of flurbiprofen was used in lieu of 0.25 g of spadicomycin, whereby pellets of flurbiprofen-phospholipid complex and a lyophilizate thereof were obtained.

EXAMPLE 7

The same procedures of Examples 1 and 2 were repeated except that 0.25 g of prostaglandin $E_1$ and 5 g of purified soybean phospholipid were used in lieu of 0.25 g of spadicomycin and 10 g of purified egg yolk phospholipid, whereby pellets of prostaglandin-hospholipid complex and a lyophilizate thereof were obtained.

While the invention has been described in detail and with reference to specific embodiments thereof, it will be apparent to one skilled in the art that various changes and modifications can be made therein without departing from the spirit and scope thereof.

What is claimed is:

1. A method of producing a water-soluble complex comprising a water-insoluble drug which is a pharmacologically active compound having a molecular weight not over 1,000 and a phospholipid, comprising the steps of (1) dissolving a water-insoluble drug and a phospholipid in an organic solvent in a ratio of 0.01 to 10 parts by weight of said drug per part by weight of said phospholipid, (2) removing the solvent by evaporation to leave behind a drug-containing phospholipid film, (3) suspending the resulting film in physiologically acceptable aqueous solution, (4) ultrasonicating the film, whereby particle diameter is adjusted to 0.2 to 2 μm, (5) centrifuging the resulting suspension at 10,000× g or more for a period of 30 minutes to 2 hours to divide it into three layers comprising an upper layer, an intermediate layer and a lower most layer, and (6) recovering the lowermost layer of the resulting sediment to yield the water-soluble complex.

2. The method according to claim 1, wherein said water-insoluble drug has a solubility in an organic solvent in the range of about 0.1 to 100 mg/ml.

3. The method according to claim 1, wherein said drug is an anticancer drug.

4. The method according to claim 3, wherein said drug is an anticancer drug is a member selected from the group consisting of spadicomycin, anthramycin, daunomycin and adriamycin.

5. The method according to claim 1, wherein said drug is an anti-inflammatory-analgesic drug.

6. The method according to claim 5, wherein said anti-inflammatory-analgesic drug is a member selected from the group consisting of flurbiprofen and acemetacin.

7. The method according to claim 1, wherein said water-insoluble drug is prostaglandin.

8. The method according to claim 1, wherein said water-insoluble drug is a lipoxygenase inhibitor.

9. The method according to claim 1, wherein said phospholipid is soybean phospholipid.

10. The method according to claim 1, wherein said phospholipid is egg yolk phospholipid.

11. The method according to claim 1, wherein an antioxidant for stabilizing said phospholipid is used in a stabilizing amount.

12. The method according to claim 1, wherein said ultrasonication is performed under ice-cooling until said suspension is in a particle size range of 0.2 to 2 μ.

13. The method according to claim 1, wherein said centrifugation is performed at 10,000× g to 30,000× g for a period of 30 minutes to 2 hours.

14. The method according to claim 13, wherein said centrifugation is carried out at 20,000 to 30,000× g for a period of 30 minutes to 2 hours.

15. The method according to claim 1 wherein said drug-phospholipid complex is further freeze-dried to provide a lyophilizate.

16. The method according to claim 15, wherein said freeze-drying is performed in the presence of a nonionic surfactant.

17. The method according to claim 15, wherein said lyophilizate is further processed into a dosage form.

18. A water-soluble complex comprising a water-insoluble drug and a phospholipid produced by the method according to claim 1.

19. The complex according to claim 18, wherein said water-insoluble drug has a solubility in an organic solvent in the range of about 0.1 to 100 mg/ml.

20. The complex according to claims 18 or 19, wherein said drug has a molecular weight not over 1000.

21. The complex according to claim 18, wherein said drug is an anticancer drug.

22. The complex according to claim 21, wherein said anticancer drug is a member selected from the group consisting of spadicomycin, anthramycin, daunomycin and adriamycin.

23. The complex according to claim 18, wherein said drug is an anti-inflammatory-analgesic drug.

24. The complex according to claim 23, wherein said anti-inflammatory-analgesic drug is a member selected from the group consisting of flurbiprofen and acemetacin.

25. The complex according to claim 18, wherein said drug is a prostaglandin.

26. The complex according to claim 18, wherein said drug is a lipoxygenase inhibitor.

27. The complex according to claim 18, wherein said phospholipid is soybean phospholipid.

28. The complex according to claim 18, wherein said phospholipid is egg yolk phospholipid.

29. The complex according to claim 18, which is in the form of a lyophilizate.

* * * * *